United States Patent [19]
Brugger et al.

[11] Patent Number: 5,922,162
[45] Date of Patent: Jul. 13, 1999

[54] GAS-PERMEABLE PATHOGEN-RESISTANT LABYRINTHINE SEAL AND METHOD FOR MAKING LABYRINTHINE SEAL

[75] Inventors: James M. Brugger, Newburyport, Mass.; Teresa L. Oberbreckling, Bailey, Colo.

[73] Assignee: COBE Laboratories, Inc., Lakewood, Colo.

[21] Appl. No.: 08/993,218

[22] Filed: Dec. 18, 1997

Related U.S. Application Data

[63] Continuation-in-part of application No. 08/873,553, Jun. 12, 1997, abandoned, which is a continuation of application No. 08/577,715, Dec. 22, 1995, abandoned, which is a division of application No. 08/577,057, Dec. 22, 1995, abandoned, which is a division of application No. 08/474,945, Jun. 7, 1995, abandoned.

[51] Int. Cl.⁶ ........................................ B32B 31/00
[52] U.S. Cl. .................... 156/275.1; 156/272.2; 156/290; 428/134; 428/136
[58] Field of Search .............. 156/272.2, 275.1, 156/379.6, 379.8, 380.2, 380.6, 580, 581, 583.1, 583.4, 290; 428/98, 131, 134, 136

[56] References Cited

U.S. PATENT DOCUMENTS

| | | | |
|---|---|---|---|
| 3,122,466 | 2/1964 | Shabram | 156/583.4 X |
| 4,000,029 | 12/1976 | Michaels | 156/510 |
| 4,057,144 | 11/1977 | Schuster | 206/439 |
| 4,154,342 | 5/1979 | Wallace | 206/439 |
| 4,177,100 | 12/1979 | Pennington | 156/157 |
| 4,296,862 | 10/1981 | Armentrout et al. | 206/439 |
| 4,761,197 | 8/1988 | Christine et al. | 156/290 |
| 4,824,354 | 4/1989 | Keaton | 425/345 |
| 4,981,006 | 1/1991 | Caenazzo et al. | 53/388 |
| 5,058,361 | 10/1991 | Schmacher | 53/370.9 |
| 5,149,393 | 9/1992 | Hutchinson et al. | 156/555 |
| 5,164,208 | 11/1992 | Thomas, Jr. | 425/396 |
| 5,266,150 | 11/1993 | Miller | 156/583.4 |
| 5,268,058 | 12/1993 | Cornwell | 156/583.1 |
| 5,312,507 | 5/1994 | Miller | 156/290 |

OTHER PUBLICATIONS

Advertisement for Doboy Packaging Machinery from Food & Drug Packaging (Aug. 1995).

Frederick C. Neidhardt, John L. Ingraham, and Moselio Schaechter, "Physiology of the Bacterial Cell A Molecular Approach," 1990, pp. 183–196.

Automated Packaging Systems, Introducing the Autobag HS–100 EXCEL. The next generation of packaging technology, date unknown.

Drawing headed "Maze Seal (Maze)" believed to be an internal document of Automated Packaging Systems, date unknown.

*Primary Examiner*—James Sells
*Attorney, Agent, or Firm*—Bruce R. Winsor

[57] ABSTRACT

A gas-permeable, pathogen-resistant seal for sealing packages containing medical products is described. The seal comprises a labyrinthine passage, preferably formed in two dimensions, through which bacteria cannot pass. The seal functions to block the passage of bacteria without an additional bacteria blocking material. A method for making the subject seal using heat sealing techniques is also described.

21 Claims, 8 Drawing Sheets

GAS-PERMEABLE PATHOGEN-RESISTANT LABYRINTHINE SEAL AND METHOD FOR MAKING LABYRINTHINE SEAL

This application is a continuation-in-part of application Ser. No. 08/873,553 filed Jun. 12, 1997, abandoned, which is continuation of Ser. No. 08/577,715 filed Dec. 22, 1995, abandoned, which is a division of Ser. No. 08/577,057 filed Dec. 22, 1995, abandoned, which is a division of Ser. No. 08/474,945 filed Jun. 7, 1995, abandoned.

FIELD OF THE INVENTION

The present invention relates generally to bacteria barriers useful in packages for maintaining substances, supplies, or equipment in a sterile environment, and specifically, relates to a gas-permeable, pathogen-resistant labyrinthine seal formed in two dimensions to seal the contents contained within a package in a sterile environment.

BACKGROUND OF THE INVENTION

Heat-sealed plastic bags are well known in the packaging industry. Such bags have been used to seal foods, medical supplies and equipment, pharmaceuticals, health care products and the like. In many cases, the bags are used to reduce product contamination and deterioration by preventing entry of bacteria or other pathogens. The bags can also serve the function of evidencing product tampering. In the medical supply and equipment industries, the bags are frequently gas-permeable.

Designs (i.e., shape, length and diameter) of tortuous or labyrinthine passages effective in substantially preventing bacterial and viral access are well known in the art. For instance, one such design is a tortuous passage integrated into a wall or side panel of a sterile package or container, while utilizing a separate means for finally sealing the package and thus protecting its contents. Another prior art design includes a tortuous passage incorporated into a seal, but requires an additional material as noted above, such as Tyvek™ paper, to prevent entry of contaminants. The Tyvek™ or other surgical latex coated paper acts as a three-dimensional barrier used in conjunction with weld-type seals. In addition, the prior art designs generally utilize labyrinthine seals formed in three dimensions, such as by carefully aligning, overlapping and pressing together a pair of discs, a time consuming and expensive process, which necessarily would raise the price of the final product.

One prior art heat-sealed, gas-permeable bag used in packaging plastic medical products consists of a single rectangular plastic piece that is folded at about the middle of its length, and heat sealed along the three open edges to form an approximately square sealed bag. To provide gas permeability, the rectangular plastic piece, prior to the folding and sealing steps, is perforated at several places in a band spanning the width of the bag. To prevent entry of bacteria, a strip of Tyvek™ paper is heat sealed over an area that encompasses the perforations. At least two heat-sealing steps are performed to secure the barrier paper to the bag. Tyvek™ and other surgical latex coated papers in this application act as a three-dimensional barrier that operates in conjunction with weld seals.

The bag is required to be gas-permeable because sterilization of the medical product sealed in the bag can result in the accumulation of toxic or malodorous gases in the bag. If sterilization is via gamma irradiation, the released malodorous gases should be vented. If sterilization is with ethylene oxide, the gas must first diffuse into the bag to sterilize the product, and must later diffuse out of the bag to reduce potentially toxic gas to acceptable levels. Some manufacturers sterilize their medical products in sealed bags with slits or pinholes to provide gas exchange. While such bags can be less expensive to manufacture, the likelihood of contamination with pathogens is much greater with products packaged in this manner.

In the medical supply and other industries, there is a continuing need to reduce packaging costs without compromising product sterility. The subject invention can reduce packaging costs while maintaining permeability of a bag or other package to gases and maintaining product sterility.

SUMMARY OF THE INVENTION

The present invention broadly comprises a gas-permeable, pathogen-resistant seal for maintaining substances, such as supplies or equipment in a sterile environment, such as a flexible bag or other package, which serves as a bacterial, microbial, and contamination barrier between the exterior of the package and the contents contained therein. The labyrinthine seal comprises a labyrinthine passage connecting the interior of the package with the exterior which is sufficiently tortuous to keep substantially all bacteria and viruses from entering the interior of the package, while simultaneously serving as a venting mechanism by allowing a free exchange of gasses through the passage between the interior to the exterior of the package. In a preferred embodiment, the passage is formed in two dimensions upon sealing of first and second portions of a flexible bag or other package. In one embodiment, the passage has at least two angles of no more than about 90 degrees each. In one preferred embodiment, each of the two angles is about 90 degrees. In another embodiment, the tortuous passage can be curved.

The seal of the present invention is adapted to prevent entry of bacteria under standard air pressure and atmospheric humidity conditions, but more specifically, is intended to prevent entry of bacteria under the normal pressure conditions and changing differentials associated with all distributions environments, for instance, air cargo, ocean, trucking, etc. In this regard, the labyrinthine seal is useful in sterilizing the contents of the package by a number of known methods, including without limitation, autoclave, E-beam, EtO, and Gamma sterilization.

It is also contemplated that the labyrinthine seal be employed with a thermoformed tray or lidstock package to finally seal in a sterile and gas permeable environment medical supplies or other equipment therein. In this application, a non-permeable lidstock is applied and sealed to a thermoformed tray using the labyrinthine seal around the perimeter of the tray. Tray materials include, without limitations, PVC, PETG, HDPE, LDPE, PET, polypropylene, and coextruded materials.

The subject invention also comprises a method of making a gas-permeable, pathogen-resistant labyrinthine seal, comprising closing an opening in a package or flexible bag by joining first and second portions of the package or bag and sealing the portions together to define a labyrinthine passage in two dimensions connecting the interior of the package or bag with the exterior. In one embodiment, the labyrinthine passage is formed with at least two angles, each angle being no more than about 90 degrees. The labyrinthine passage can also be a curved section through which pathogens cannot pass.

Compared to one of the prior art methods described herein, the subject method has the advantage that it does not use an additional barrier material such as Tyvek™ or other paper. Eliminating materials from a manufacturing process can reduce associated costs such as the costs of material inventory and quality control. Elimination of a material from a product can also simplify the manufacturing process and can enhance the recyclability of the bag as assembly of the bag prior to recycling is eliminated.

In addition, the process of forming the labyrinthine seal of the present invention in two rather than three dimensions is less complex, requiring less time and money to create a less expensive final product.

Unlike prior art designs, the seal of the subject invention is contemplated as a final, closing seal to the bag or package after the contents have been loaded into the interior of the bag. That is, the labyrinthine seal of the present invention not only allows an exchange of gases and protection from the entry of bacteria, as is described in prior art bags and packages, but is an integral part of the bag or package itself created when adjoining or overlapping portions of the bag or package are fused together as described below.

DETAILED DESCRIPTION OF THE PREFERRED EMBODIMENT(S)

A more complete understanding of the invention may be obtained by reference to the drawings.

Figure 1:
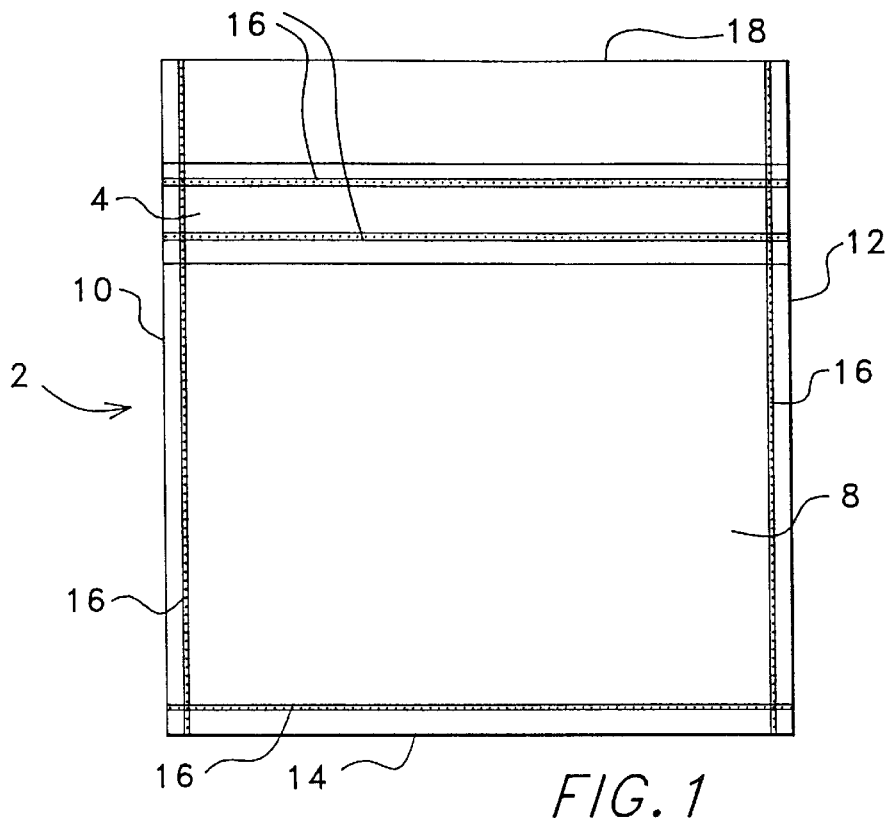
FIG. 1 is an elevation view of a prior art bag.
Figure 2:
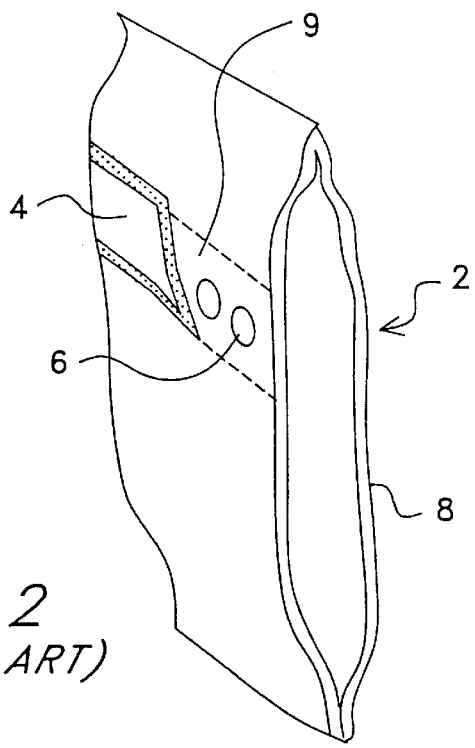
FIG. 2 is a partially cutaway sectional perspective view of a prior art bag.

FIGS. 1 and 2 illustrate a prior art bag 2 comprising a thermoplastic material which is gas-permeable and bacteria resistant due to a seal formed by perforations 6 and covered with Tyvek™ paper 4. The bag 2 is formed by perforating a rectangular sheet 8 of plastic within a defined band 9 across the width of the rectangle 8. A strip of Tyvek™ paper 4 is then laid over and sealed 16 to the plastic. The rectangle 8 is then folded approximately midway 18 along its length and sealed 16 along the two side edges 10 and 12. After product (not shown) is loaded into the bag 2, bottom edge 14 is sealed 16.

Figure 3:
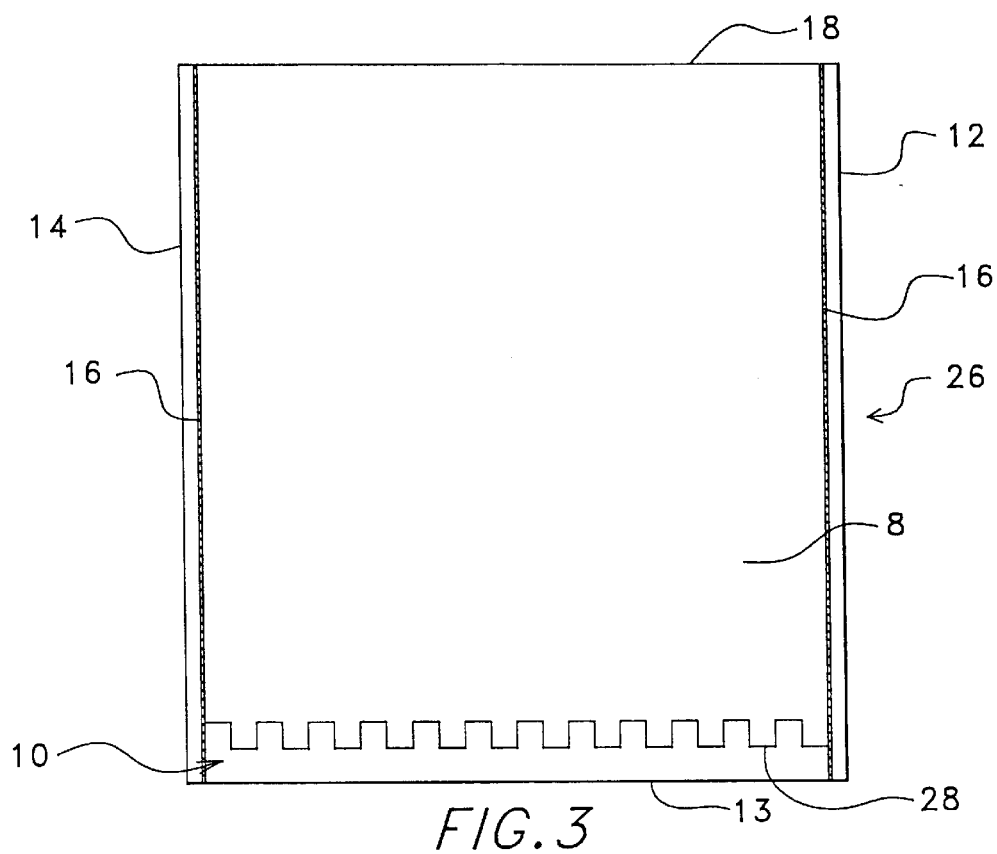
FIG. 3 is an elevational view of one embodiment of the subject invention.

FIG. 3 illustrates a first embodiment of the subject invention 10 used to seal one edge of a flexible bag 26. Bag 26 is formed by folding a rectangular sheet 8 of plastic at approximately midway 18 along its length. The side edges 12, 14, are sealed 16 by a prior art method. Bottom edge 13 is sealed using the subject invention. The labyrinthine passage is symbolically indicated by reference number 28. Product (not shown) can be loaded into the bag 26 usually with the two side edges 12, 14, or one side edge 12 or 14 and the bottom edge 13 sealed, followed by sealing of the final edge 12, 14, or 13. Preferably, the final seal of the bag occurs after the product is loaded by applying the labyrinthine seal 10 to the remaining open edge.

Figure 4:
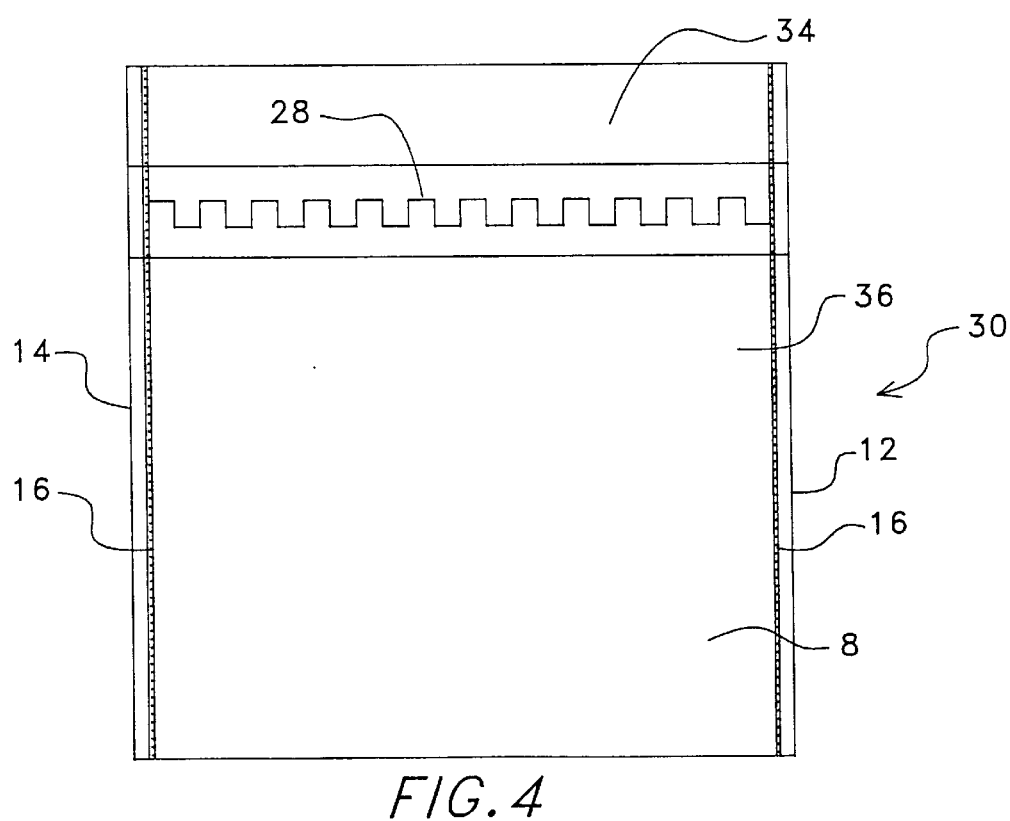
FIG. 4 is an elevational view of another embodiment of the subject invention.
Figure 6A:
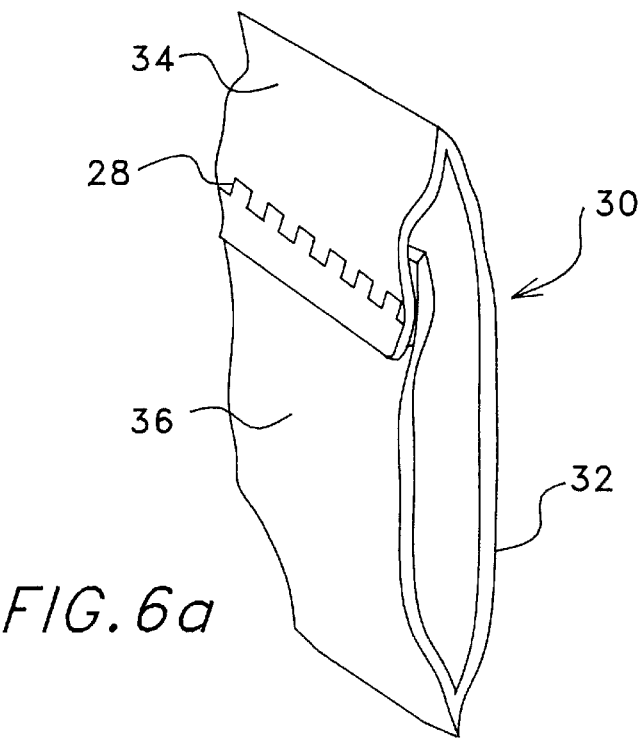
FIGS. 6a and 6b are sectional perspective views of different embodiments of the bag illustrated in FIG. 4.

FIGS. 4 and 6 illustrate other embodiments of the subject invention 10 utilized in a bag 30 formed by folding a rectangular sheet 8 of plastic such that a back panel 32, and overlapping front upper panel 34 and front lower panel 36 are formed. Side edges 12, 14 are sealed 16 by a prior art method. In FIGS. 4 and 6a, overlapping front upper panel 34 and lower front panel 36 have been sealed to create a labyrinthine passage symbolized by reference number 28. In FIG. 6a, product (not shown) is loaded into the bag 30 between overlapping upper front panel 34 and lower front 35 panel 36 prior to sealing.

Figure 6B:
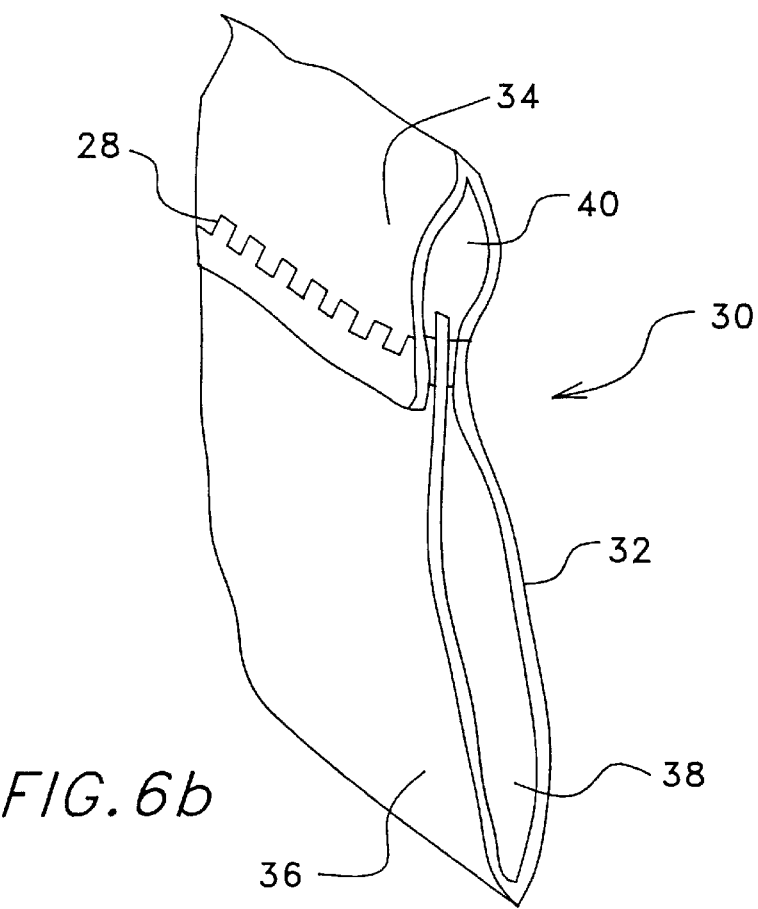

In FIG. 6b, overlapping front upper panel 34, lower front panel 36, and back panel 32 are sealed 28 together. In FIG. 6b, product (not shown) is loaded into the bag 30 between the overlapping upper front panel 34 and lower front panel 36 and positioned in space 38 prior to sealing of upper and lower front panels 34, 36, and back panel 32. The FIG. 6b embodiment more than doubles the length that bacteria must travel in the labyrinthine passage 28 due to the sealing together of three layers of plastic, 34, 36 and 38 and the creation of space 40.

Figure 5:
FIG. 5 illustrates four patterns of labyrinthine passages.

FIG. 5 illustrates representative patterns 52 that can be used for the labyrinthine passage. The seal itself creates these labyrinthine forms. A preferred form of labyrinthine pattern is shown in FIGS. 7, 8, 9a and 9b. As is known to persons of skill in the art, a pathway having at least two angles of about 90 degrees or less or having curves can prevent passage of bacteria.

Figure 7:
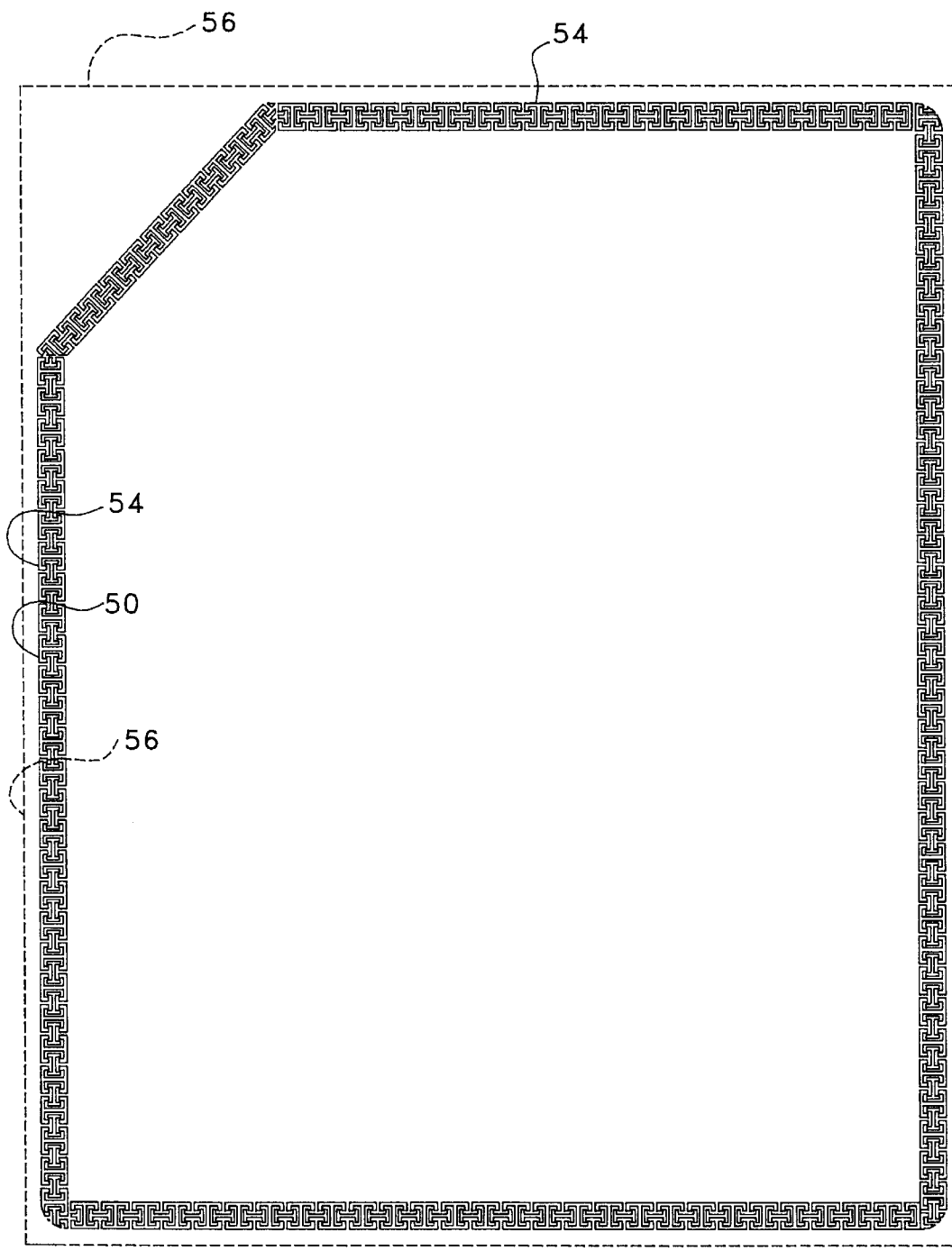
FIG. 7 illustrates the subject invention used in a thermo-formed tray and lidstock application.

FIG. 7 illustrates the labyrinthine seal of the present invention 50 utilizing the preferred labyrinthine pattern form, sealing a non-permeable lidstock, the perimeter of which is designated by reference number 54, to a thermoformed tray, the perimeter of which is indicated by dashed line 56. The seal 50 is preferably applied about the perimeter of the tray 56 after the contents (not shown), such as medical supplies and the like, are placed therein.

Figure 8:
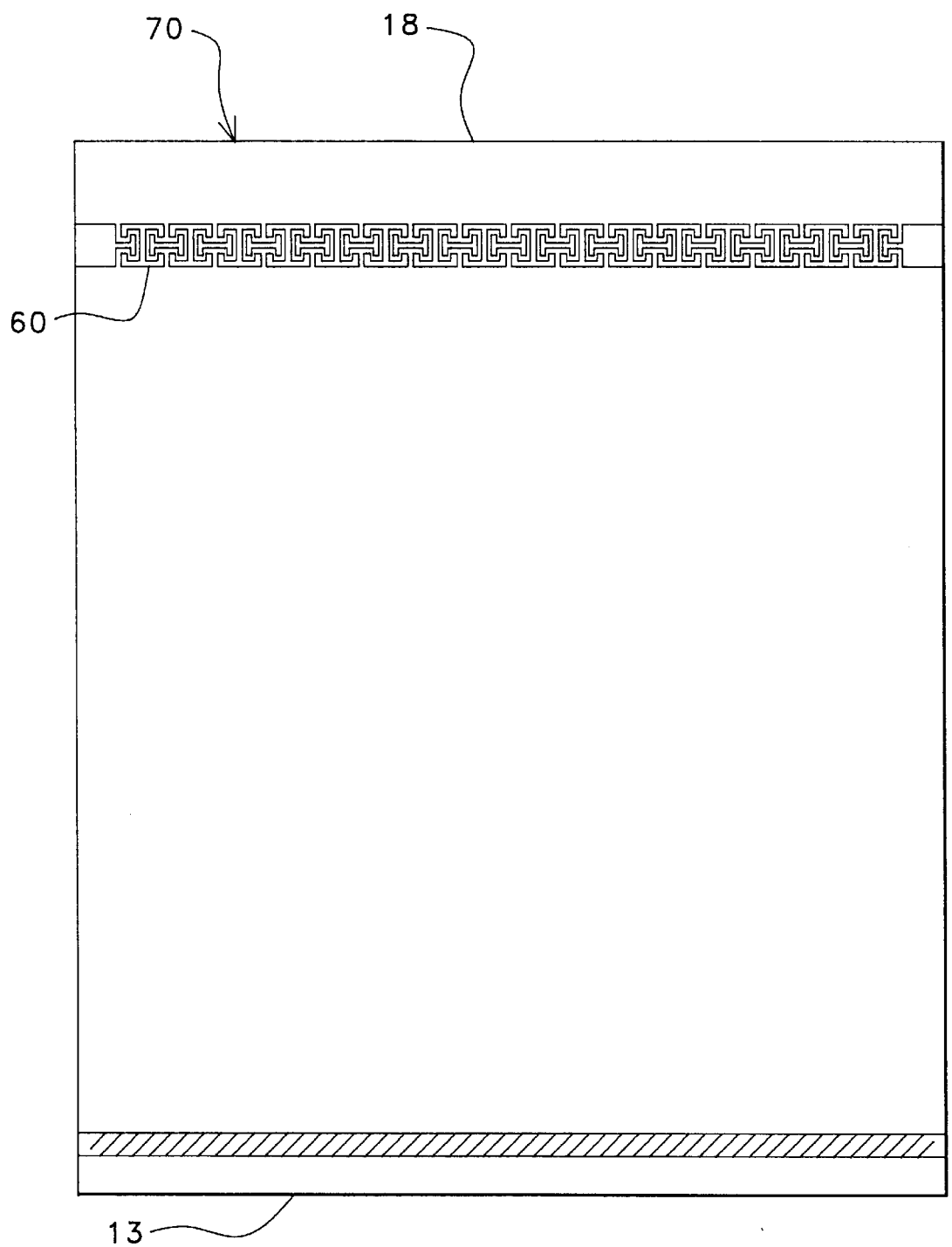
FIG. 8 illustrates the subject invention used in a flat polybag dispensed from a roll.

FIG. 8 shows the preferred form of the labyrinthine passage in the labyrinthine seal of the present invention 60 used in yet another application, in a flat polybag, or "bag-on-a-roll" type flexible bag 70. In this application, the bottom edge 13 are factory or supplier sealed using a standard heat seal technique, and the tortuous, labyrinthine seal 60 is applied to the upper edge 18 after loading the product into the bag 70. Alternatively, the vendor seal could be a tortuous path design, with the production seal being a standard type heat seal. In this application, the bag 70 is produced from blown/extruded film tubing which does not have side seals. This application also extends to flat pouches with weld seals on three sides, all or some of which are a tortuous path.

Figure 9A:
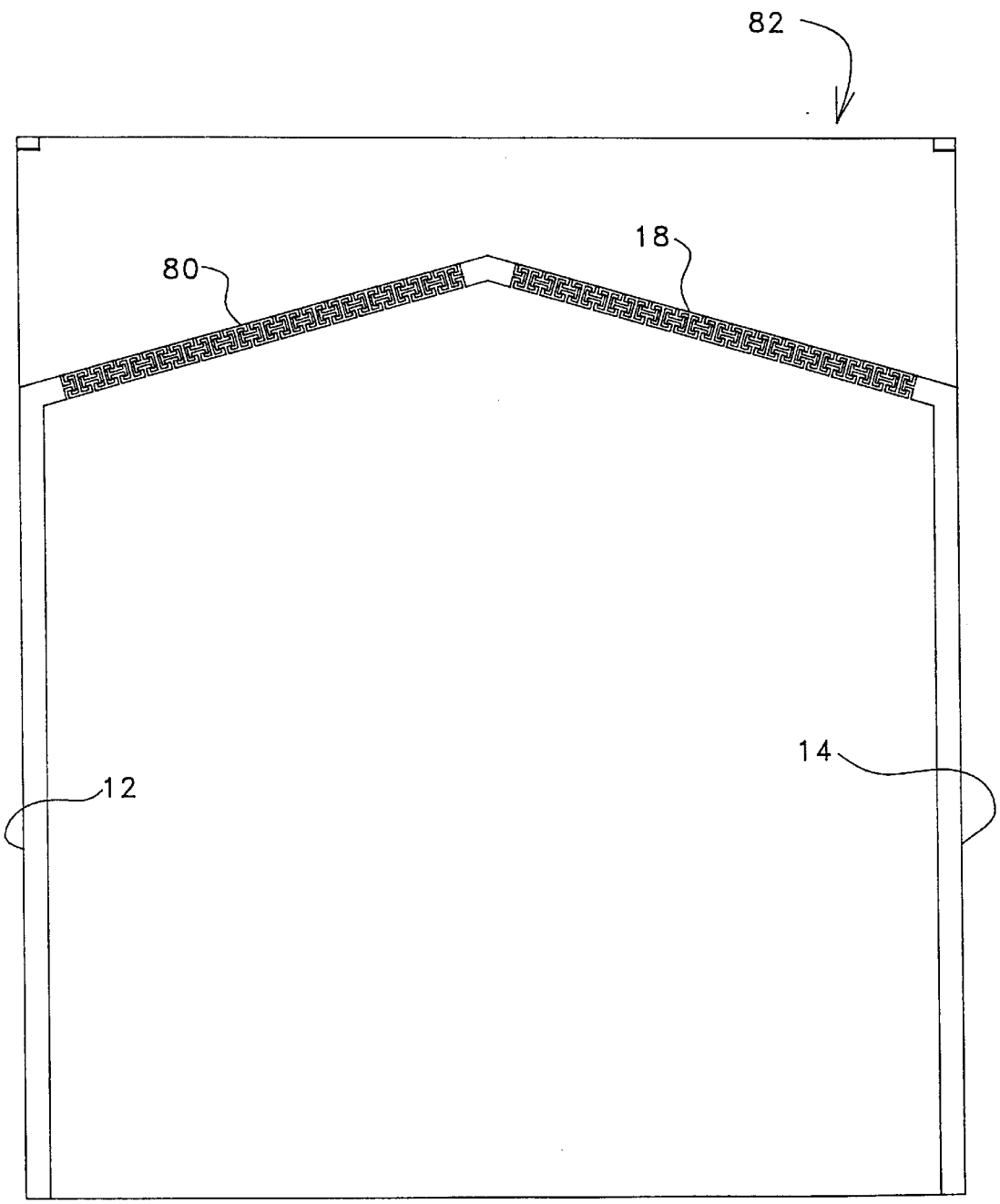
FIGS. 9a and 9b illustrate the subject invention used in a chevron-type bag on one or more edges.
Figure 9B:
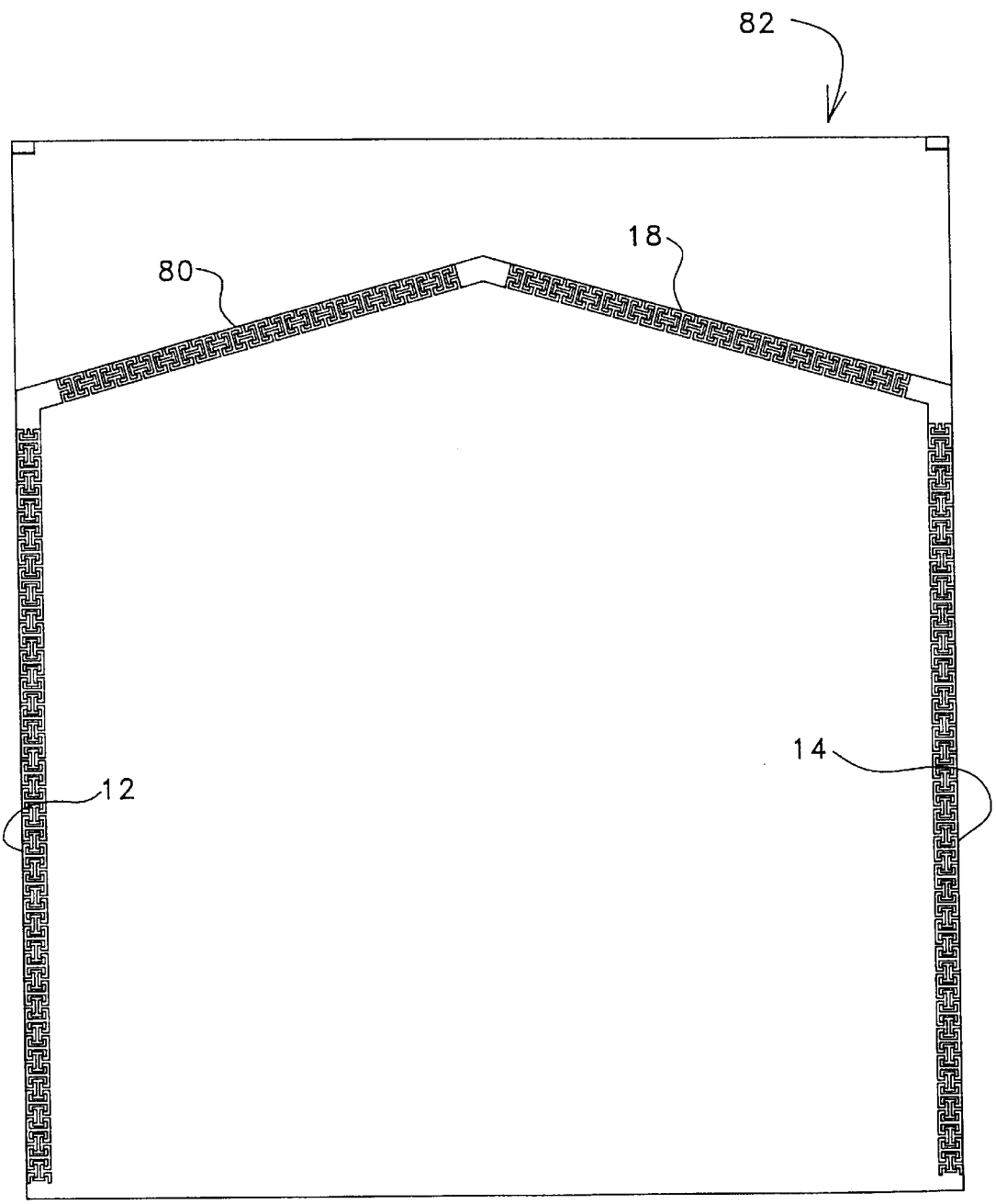

FIGS. 9a and 9b illustrate the preferred embodiment of the labyrinthine passage in the seal 80 used to seal a chevron-type pouch 82, where the tortuous path seal 80 seals on one or more edges 12, 14, 18. This application utilizes flexible or rigid films with a flexible heat seal layer.

When the labyrinthine seal of the present invention is used to seal a flexible sterile bag, the bag is typically made of thermoplastic resins such as styrene, acrylics, celluloses, polyethylenes, vinyls, nylons and fluorocarbons. In a preferred embodiment, the bag is made of polyethylene. The diameter of the passage or any leg of the passage is typically less than about 5 MM.

The subject method of creating a seal comprising a labyrinthine passage can be carried out by a variety of known methods, including without limitation, the application of heat, hot air, sonogram or ultrasound, or a radio frequency electric field to the sheets of plastic to be sealed. As is known in the art, when a radio frequency electric field is applied to thermoplastic material having a relatively high dielectric loss coefficient, heating of the two sheets of plastic results such that they melt or fuse together. In general, the labyrinthine passage can be formed by any sealing method usable on flexible plastic sheets which can be applied from the exterior of the sheets, and which will produce tightly controlled welded and unwelded zones.

In addition, the seal of the present invention can be created by extruding a pattern of adhesive to one of the substrates or by printing the pattern on the substrate via rotogravure or flexographic processes which would then, through application of pressure, heat or curing processes, create seal and bond materials.

The labyrinthine seal of the subject invention is preferably formed by a heat or radio frequency sealing apparatus. Such apparatus has platens at least one of which is embossed with a pattern that will generate the labyrinthine passage when applied to the two aligned or overlapping sheets of plastic. The seal can also be formed by an apparatus having two belts, at least one of which is embossed with the labyrinthine pattern. The belts are each mounted on wheels so that a portion of one belt is opposed and off-set from a portion of the second belt. In operation, the open edge of a plastic bag is fed between the belts, whereby the bag is sealed with a labyrinthine pattern.

It is therefore to be understood that while preferred forms of the invention have been herein set forth and described, various modifications and changes may be made in the construction and arrangement of elements and steps, as well as composition of materials, without departing from the spirit and scope of the present invention as defined by the appended claims.

What is claimed is:

1. A method of making a gas-permeable, pathogen-resistant labyrinthine seal, comprising the steps of:

closing an opening in a package by forming a labyrinthine passage in two dimensions to directly and gas permeably connect an interior and an exterior of said package, said passage having at least two angles, wherein said labyrinthine passage prevents entry of substantially all bacteria into the interior of said package under standard air pressure and atmospheric humidity conditions without use of an additional barrier material.

2. The method of claim 1 wherein the step of closing comprises applying heat.

3. The method of claim 1, wherein the labyrinthine passage comprises at least two angles, each said angle being no more than about 90 degrees.

4. The method of claim 3, wherein the labyrinthine passage comprises at least two angles, each said angle being about 90 degrees.

5. The method of claim 1, wherein the labyrinthine passage comprises a curved section through which bacteria cannot pass.

6. The method of claim 1, wherein the opening comprises at least two aligned sheets of plastic at an open edge of said package.

7. The method of claim 1, wherein the opening comprises overlapping upper and lower plastic panels.

8. The method of claim 1, wherein the step of closing comprises applying a radio frequency electric field.

9. In a gas-permeable, pathogen-resistant flexible bag comprising a first sheet portion of flexible material, a second sheet portion of flexible material at least partially overlapping said first sheet portion at an opening of said bag and gas impermeably fixed to said first sheet portion to form a bag having an interior and an exterior directly connected through said opening, a gas-permeable, pathogen-resistant seal, comprising:

a labyrinthine passage formed in two dimensions and defined by affixing said first sheet portion to said second sheet at said at least partial overlap at the opening connecting the interior and the exterior of the bag, said labyrinthine passage directly and gas permeably connecting the interior of the bag with the exterior of the bag without use of an additional barrier material.

10. The seal of claim 9, wherein the labyrinthine passage comprises a passage having at least two angles of no more than 90 degrees each.

11. The seal of claim 10, wherein the labyrinthine passage has at least two angles, said angles being about 90 degrees each.

12. The seal of claim 9, wherein the labyrinthine passage comprises a curved portion.

13. The seal of claim 9, wherein the labyrinthine passage prevents entry of substantially all bacteria under standard air pressure and atmospheric humidity conditions.

14. The seal of claim 9, wherein the labyrinthine passage prevents entry of substantially all bacteria under pressures typical in distribution environments.

15. A gas-permeable, pathogen-resistant labyrinthine seal, comprising:

a labyrinthine passage formed in two dimensions to directly and gas permeably connect an interior and an exterior of a package, said passage having at least two angles, wherein said labyrinthine passage prevents entry of substantially all bacteria into the interior of said package without use of an additional barrier material.

16. The seal of claim 15, wherein the labyrinthine passage comprises a passage having at least two angles of no more than 90 degrees each.

17. The seal of claim 16, wherein the labyrinthine passage has at least two angles, said angles being about 90 degrees each.

18. The seal of claim 15, wherein the labyrinthine passage comprises a curved portion.

19. The seal of claim 15, wherein the labyrinthine passage prevents entry of substantially all bacteria under standard air pressure and atmospheric humidity conditions.

20. The seal of claim 15, wherein the labyrinthine passage prevents entry of substantially all bacteria under pressures typical in distribution environments.

21. The seal of claim 15, wherein the package is a tray with lidstock cover.

* * * * *